US009649403B2

(12) United States Patent
Sahoo et al.

(10) Patent No.: US 9,649,403 B2
(45) Date of Patent: May 16, 2017

(54) PROCESS FOR PREPARING CURCUMIN ENCAPSULATED CHITOSAN ALGINATE SPONGE USEFUL FOR WOUND HEALING

(75) Inventors: Sanjeeb Kumar Sahoo, Bhubaneswar (IN); Mohanty Chandana, Bhubaneswar (IN)

(73) Assignee: Institute of Life Sciences, Orissa (IN)

( * ) Notice: Subject to any disclaimer, the term of this patent is extended or adjusted under 35 U.S.C. 154(b) by 0 days.

(21) Appl. No.: 13/823,437

(22) PCT Filed: Dec. 15, 2010

(86) PCT No.: PCT/IN2010/000813
§ 371 (c)(1),
(2), (4) Date: Mar. 14, 2013

(87) PCT Pub. No.: WO2012/056465
PCT Pub. Date: May 3, 2012

(65) Prior Publication Data
US 2013/0171215 A1 Jul. 4, 2013

(30) Foreign Application Priority Data
Oct. 27, 2010 (IN) .......................... 1189/KOL/2010

(51) Int. Cl.
| | | |
|---|---|---|
| A61L 15/44 | (2006.01) |
| A61L 15/28 | (2006.01) |
| A61F 13/00 | (2006.01) |
| A61K 9/00 | (2006.01) |
| A61K 9/19 | (2006.01) |
| A61K 9/50 | (2006.01) |
| A61K 31/121 | (2006.01) |
| A61K 31/722 | (2006.01) |
| A61K 31/734 | (2006.01) |

(52) U.S. Cl.
CPC ........ *A61L 15/44* (2013.01); *A61F 13/00012* (2013.01); *A61F 13/00063* (2013.01); *A61F 13/00991* (2013.01); *A61K 9/0014* (2013.01); *A61K 9/19* (2013.01); *A61K 9/5036* (2013.01); *A61K 9/5089* (2013.01); *A61K 31/121* (2013.01); *A61K 31/722* (2013.01); *A61K 31/734* (2013.01); *A61L 15/28* (2013.01); *A61F 2013/0091* (2013.01); *A61F 2013/00927* (2013.01)

(58) Field of Classification Search
CPC ...... A61K 9/0014; A61K 9/19; A61K 9/5036; A61K 9/5089; A61K 31/722; A61K 31/734; A61K 31/121; A61L 15/44; A61L 15/28; A61F 13/00012; A61F 13/00063; A61F 13/00991; A61F 2013/0091; A61F 2013/00927
USPC ................. 424/400; 427/244; 514/560, 679
See application file for complete search history.

(56) References Cited

U.S. PATENT DOCUMENTS 5,836,970 A * 11/1998 Pandit .......................... 606/213

OTHER PUBLICATIONS

Pereira et al. Effect of oleic and linoleic acids on the inflammatory phase of wound healing in rats. Cell Biochem Func 26:197-204, 2008.*
Goethals, E, Bansal, V and Bhargava, S 2010, 'Templated synthesis of chitosan nanocapsules with controllable shell thickness and porosity', in Mark J. Briggs (ed.) Chemeca 2010, Melbourne, Australia, Sep. 27-29, 2010, pp. 1-10.*
Cui et al. Enhancement of oral absorption of curcumin by self-microemulsifying drug delivery systems. International Journal of Pharmaceutics 371 (2009) 148-155.*
Aggarwal et al., Anticancer Potential of Curcumin: Preclinical and Clinical Studies, Anticancer Research, 2003, 363-398, vol. 23.
Aggarwal et al. Curcumin (Diferuloylmethane) Down-Regulates Expression of Cell Proliferation and Antiapoptotic and Metastatic Gene Products through Suppression of I-Kappa-B-Alpha Kinase and Akt Activation, Molecular Pharmacology, 2006, 195-206, vol. 69.
Aggarwal and Sung, Pharmacological Basis for the Role of Curcumin in Chronic Diseases: an Age-old Spice with Modern Targets, Trends in Pharmacological Sciences, 2008, 85-94, vol. 30, No. 2.
Anand et al., Bioavailability of Curcumin: Problems and Promises, Molecular Pharmaceutics, 2007, 807-818, vol. 4, No. 6.
Dai et al., Chitosan-Alginate Sponge: Preparation and Application in Curcumin Delivery for Dermal Wound Healing in Rat, Journal of Biomedicine and Biotechnology, 2009, 1-8.
Hwang et al., Chitinous Materials Inhibit Nitric Oxide Production by Activated RAW 264.7 Macrophages, Biochemical and Biophysical Research Communications, 2000, 229-233, vol. 271.
Gopinath et al., Dermal Wound Healing Processes with Curcumin Incorporated Collagen Films, Biomaterials, 2004, 1911-1917, vol. 25.
Gottrup, Oxygen in Would Healing and Infection, World Journal of Surgery, 2004, 312-315, vol. 28.
Goycoolea et al., Chitosan-Alginate Blended Nanoparticles as Carriers for the Transmucosal Delivery of Macromolecules, Biomacromolecules, 2009, 1736-1743, vol. 10.
Kim et al., Naturally Occurring Phytochemicals for the Prevention of Alzheimer's Disease, Journal of Neurochemistry, 2010, 1415-1430, vol. 112.
Lai et al., The Preparation and Chartacterisation of Drug-Loaded Alginate and Chitosan Sponges, International Journal of Pharmaceutics, 2003, 175-181, vol. 251.

(Continued)

*Primary Examiner* — Clinton Brooks
*Assistant Examiner* — Yih-Horng Shiao
(74) *Attorney, Agent, or Firm* — The Webb Law Firm

(57) ABSTRACT

A process for preparing curcumin encapsulated chitosan alginate sponge comprising the steps of: incorporating curcumin in a fluid phase of oleic acid; subjecting the mixture to a step of emulsification with chitosan solution by homogenization; emulsifying the resultant solution with alginate solution by homogenization; lyophilizing the final emulsion by freeze drying to produce curcumin loaded AC sponge.

14 Claims, 5 Drawing Sheets

(56) References Cited

OTHER PUBLICATIONS

Figure 1:
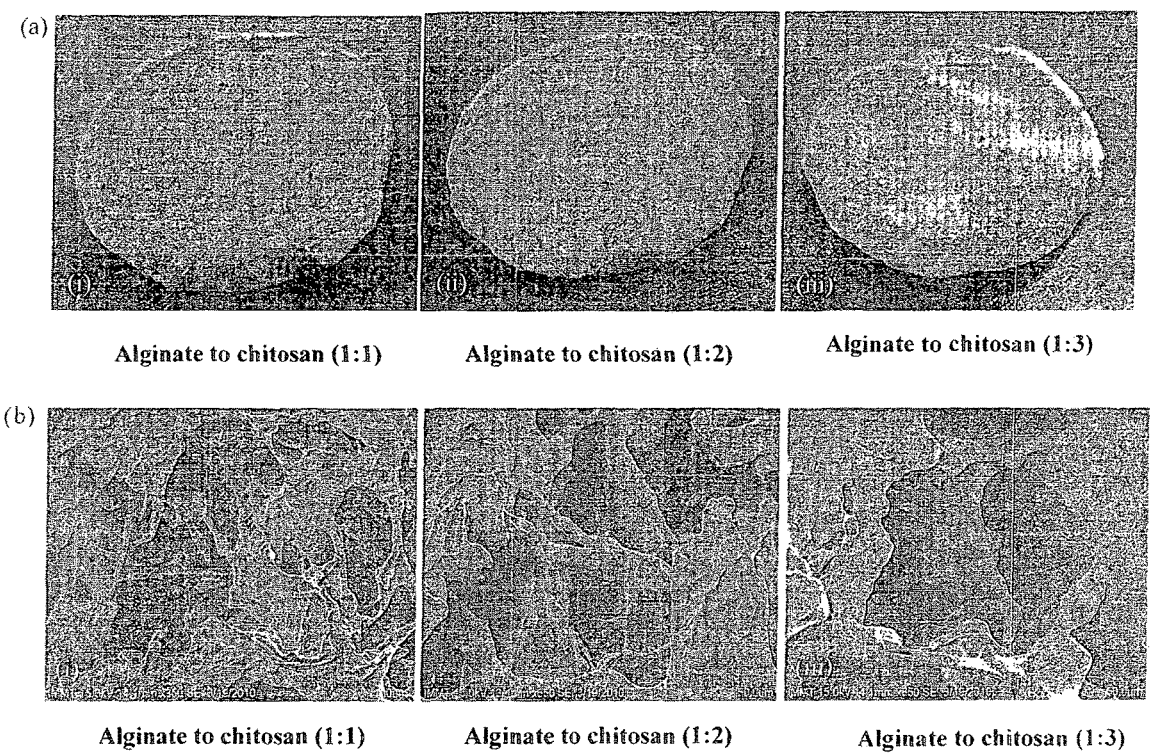

Mohanty and Sahoo, The In Vitro Stability and In Vivo Pharmacokinetics of Curcumin Prepared as an Aqueous Nanoparticulate Formulation, Biomaterials, 2010, 6597-6611, vol. 31.
Panchatcharam et al., Curcumin Improves Wound Healing by Modulating Collagen and Decreasing Reactive Oxygen Species, Molecular and Cellular Biochemistry, 2006, 87-96, vol. 290.
Sidhu et al., Curcumin Enhances Wound Healing in Streptozotocin Induced Diabetic Rats and Genetically Diabetic Mice, Wound Repair and Regeneration, 1999, 362-374, vol. 7, No. 5.
Ueno et al., Accelerating Effects of Chitosan for Healing at Early Phase of Experimental Open Wound in Dogs, Biomaterials, 1999, 1407-1414, vol. 20.
Ueno et al., Topical Formulations and Wound Healing Applications of Chitosan, Advanced Drug Delivery Reviews, 2001, 105-115, vol. 52.
Yallapu et al., Beta-Cyclodextrin-Curcumin Self-Assembly Enhances Curcumin Delivery in Prostate Cancer Cells, Colloids and Surfaces B: Biointerfaces, 2010, 113-125, vol. 79.

* cited by examiner

PROCESS FOR PREPARING CURCUMIN ENCAPSULATED CHITOSAN ALGINATE SPONGE USEFUL FOR WOUND HEALING

FIELD OF THE INVENTION

This invention relates to a process for preparing curcumin encapsulated chitosan alginate sponge useful for wound healing.

BACKGROUND OF THE INVENTION

Wound healing is a complex physiological response to the injury. It is a very systemic biological, chemical, and mechanical event where the invaded pathogens removed from the damaged wound site for complete or partial remodeling of injured tissue. In general, it precedes in a very orderly and efficient manner characterized by three interrelated dynamic and overlapping phases, namely, inflammatory phase (consisting the establishment of homeostasis and inflammation; proliferative phase (consisting of granulation, contraction and epithelialisation) and finally the remodeling phase [1-3]. However, in severe pathologic conditions this cascade healing process is lost and the wounds are locked into a state of chronic inflammation characterized by abundant neutrophil infiltration with associated release of inflammatory mediators including reactive oxygen species, reactive nitrogen species and their derivatives. These radicals will result in oxidative stress leading to lipid peroxidation, DNA breakage, and enzyme inactivations ultimately cause local and distant pathophysiological inflammatory effects [1,4]. Mitigation of this dysregulated chronic inflammation (the major cause of impaired wound healing) and finding a safe and efficacious anti-inflammatory agent is a frontier challenge in modern medicine. However, the role of oxidants in the pathogenesis of many inflammatory diseases suggests that antioxidant has effective strategy for therapeutic approaches to such disorders [5]. To this end, anti oxidant activities of the traditional medicine give a new horizon for better healing treatment. Topical applications of compound with free radical scavenging properties have shown significant improvement in wound healing and protect tissue from oxidative damage [6]. In this regard, topical application of the upcoming anti-inflammatory drug modality of natural herbal extracts curcumin and its antioxidants properties will be certainly benefit against oxidative damage and be helpful to the better healing of the wound.

Curcumin (diferuloylmethane), a naturally occurring photochemical derived from the rhizome of turmeric (Curcuma longa). It has low intrinsic toxicity but a wide range of pharmacological activity including anti-oxidant, anti-inflammatory and anti-infective properties [7-10]. The antioxidant activity of curcumin could be attributed to the phenolic and the methoxy groups in conjunction with the 1,3-diketone conjugated diene system, for scavenging of the oxygen radicals. In this view, several in vitro and in vivo studies have demonstrated the effectiveness of curcumin to decrease the release of inflammatory cytokines like interleukin (IL)-8 and tumour necrosis factor (TNF-$\alpha$) from monocytes and macrophages and further to inhibit enzymes associates with inflammation, such as cyclo-oxygenase (COX)-2 and lipoxygenase (LOX) [11,12]. By reducing the effects of these enzymes, curcumin has shown to prevent the inflammation symptoms of many diseases like arthritis and alzheimer's disease [13]. Furthermore, various studies using rat models showed the accelerated wound healing activity of curcumin owing to its powerful anti-oxidant property. Also the ability of curcumin to assist wound healing in diabetic mice has been well demonstrated by various groups. Where curcumin treatment in diabetic wound demonstrated an increased formation of granulation tissue, neovascularization and enhanced biosynthesis of extracellular matrix (ECM) proteins, such as collagen [14]. Similarly, Panchatcharam et al in rat model demonstrated on treatment of curcumin, lipid peroxides (LPs) was decreased, while the levels of superoxide dismutase (SOD), catalase (CAT), glutathione peroxidase (GPx), activities were significantly increased exhibiting the antioxidant properties of curcumin in accelerating wound healing [4]. These observations demonstrated, curcumin has a property to scavenge free radicals, which is the major cause of inflammation during wound healing activity. Despite these unique biological activities, a major problem associated with curcumin delivery is its extreme low solubility in aqueous solubility in aqueous solutions, which limits its bioavailability and clinical efficacy [8,11,12]. One possible method to achieve this paradigm is encapsulating and delivering curcumin to inflammatory site with wound dressing sponge. This sponge are fabricated with various biocompatible and biodegradable materials, such as alginate, chitosan, gelatin and poly (ethylene glycol) and recently gained the attention in pharmaceutical and biomedical arena, as matrices for wound dressings [15,16]. Many types of polymers have been used for drug delivery system but the requirements of the biocompatibility and biodegradability have limited the choice of polymers used in clinical application. Some representatives of such materials are chitosan and alginate. Chitosan is a natural cationic mucoadhesive polymer, is biologically renewable, biodegradable, biocompatible, nonantigenic, nontoxic, and biofunctional. It can accelerate the wound healing process by enhancing the functions of inflammatory cells like macrophages and fibroblasts. It could inhibit nitric oxide production that has been shown to contribute to cytotoxicity in cell proliferation during inflammation of wound healing by the activated RAW 264.7 macrophages and allow the formation of granulation tissue with angiogenesis [17]. Furthermore, it is a penetration enhancer which can provide maximum bioavailability of delivered drug, at wound site [18]. Whereas, Alginate is an anionic polymer with additional characteristics like biocompatible, hydrophilic, and biodegradable under normal physiological conditions [18]. It is able to maintain a physiologically moist microenvironment that promotes healing and the formation of granulation tissue and achieves homeostasis [15,16]. In recent year the alginate-chitosan (AC) sponge with entrapped therapeutics are of special interest for wound healing purposes owing to their biocompatibility, biodegradaibility and ability to sustain therapeutic drug levels for prolonged periods of time. Moreover, its polymeric matrix can prevents the degradation of the drug, by protecting the encapsulated curcumin against hydrolysis and biotransformation for a longer time. Beside low aqueous solubility, the major concerned associated with curcumin delivery is its severe biodegradation and instability in biological pH. In this regard, coating the drug with large molecules, such as surfactants containing long-chain hydrocarbons, helps to provide more effective stabilization of entrapped drug in biological medium. Therefore research groups are using long chain surfactant such as oleic acid (OA) and its salt for the stabilization of various drug delivery systems.

In this scenario, the current approach was to prepare and characterize curcumin loaded sponge composed of oleic acid, chitosan and sodium alginate. We hypothesized that the hydrophobic drug curcumin would partition in to the coated oleic acid shell. Whereas, alginate and chitosan anchors at the interface of the OA shell and give the aqueous dispersibility and easy load of hydrophobic anticancer drug curcumin. Here the positively charged chitosan can be easily complexed with negatively charged polyanions sodium alginate to form porous AC sponge through the interionic interaction. The large surface area of the sponge facilitates the interaction with the healing tissue, thereby serving as a substrate for the sustained delivery of curcumin as well as improves wound healing by protecting tissues from oxidative damage. Thus, the aim of the present study is to evaluate the biological activity of the formulated curcumin-loaded AC sponge using in vitro and in vivo methods.

OBJECTS OF THE INVENTION

An object of this invention is to propose a process for preparing curcumin encapsulated chitosan alginate sponge;

Another object of this invention is to propose a curcumin encapsulated chitosan alginate sponge used for the better healing of the wound;

Further object of this invention is to propose an anti-inflammatory drug for topical application;

Still further object of this invention is to propose a natural herbal wound dressing sponge;

Another object of this invention is to propose a potential topical curcumin delivery system showing sustained release of entrapped curcumin for a longer period of its administration.

BRIEF DESCRIPTION OF THE INVENTION

According to this invention there is provided a process for preparing curcumin encapsulated chitosan alginate sponge comprising the steps of:
incorporating curcumin in a fluid phase of oleic acid;
subjecting the mixture to a step of emulsification with chitosan solution for few minutes homogenizing the resultant solution with alginate solution;
Lyophilizing the final emulsion by freeze drying to produce curcumin loaded AC sponge.

BRIEF DESCRIPTION OF THE ACCOMPANYING DRAWINGS

FIGS. 1a: shows photograph of different formulations (1:1, 1:2 and 1:3) of alginate-chitosan sponge.

Figure 2:
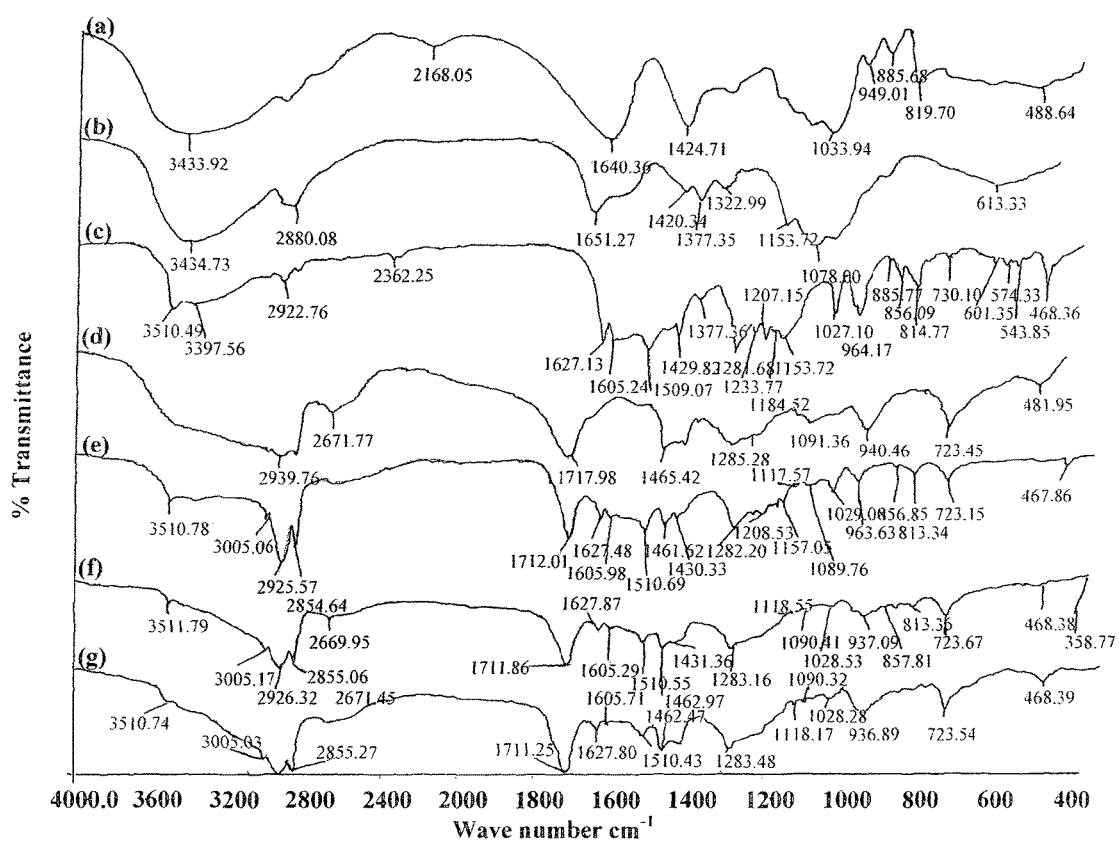

FIGS. 1b: shows Scanning electron micrograph image for sponge containing a) 1:1 alginate-chitosan b) 1:2 alginate-chitosan c) 1:3 alginate-chitosan FIG. 2: FTIR spectra of (a) Alginate (b) Chitosan (c) curcumin (d) void sponge (e) 1:1 alginate-chitosan sponge (f) 1:2 alginate-chitosan sponge (g) 1:3 alginate-chitosan sponge FIG. 3a: shows in vitro water uptake ability of different formulation of alginate-chitosan sponges.

Figure 3:
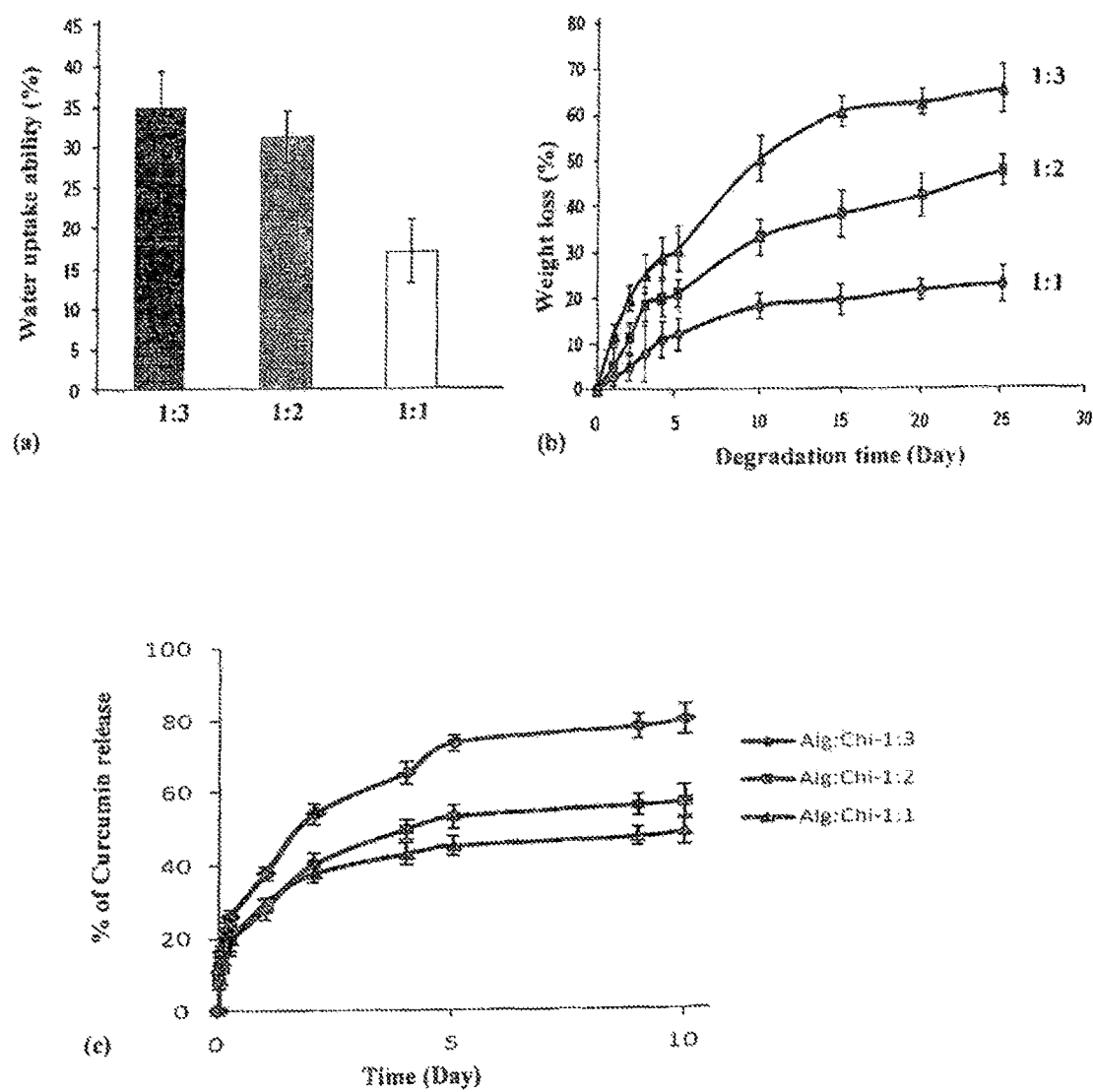

FIG. 3b: shows in vitro degradation of alginate-chitosan sponge in PBS lysozyme solution.

FIG. 3c: shows the in vitro release kinetics of curcumin from different formulation of alginate-chitosan sponge.

Figure 4:
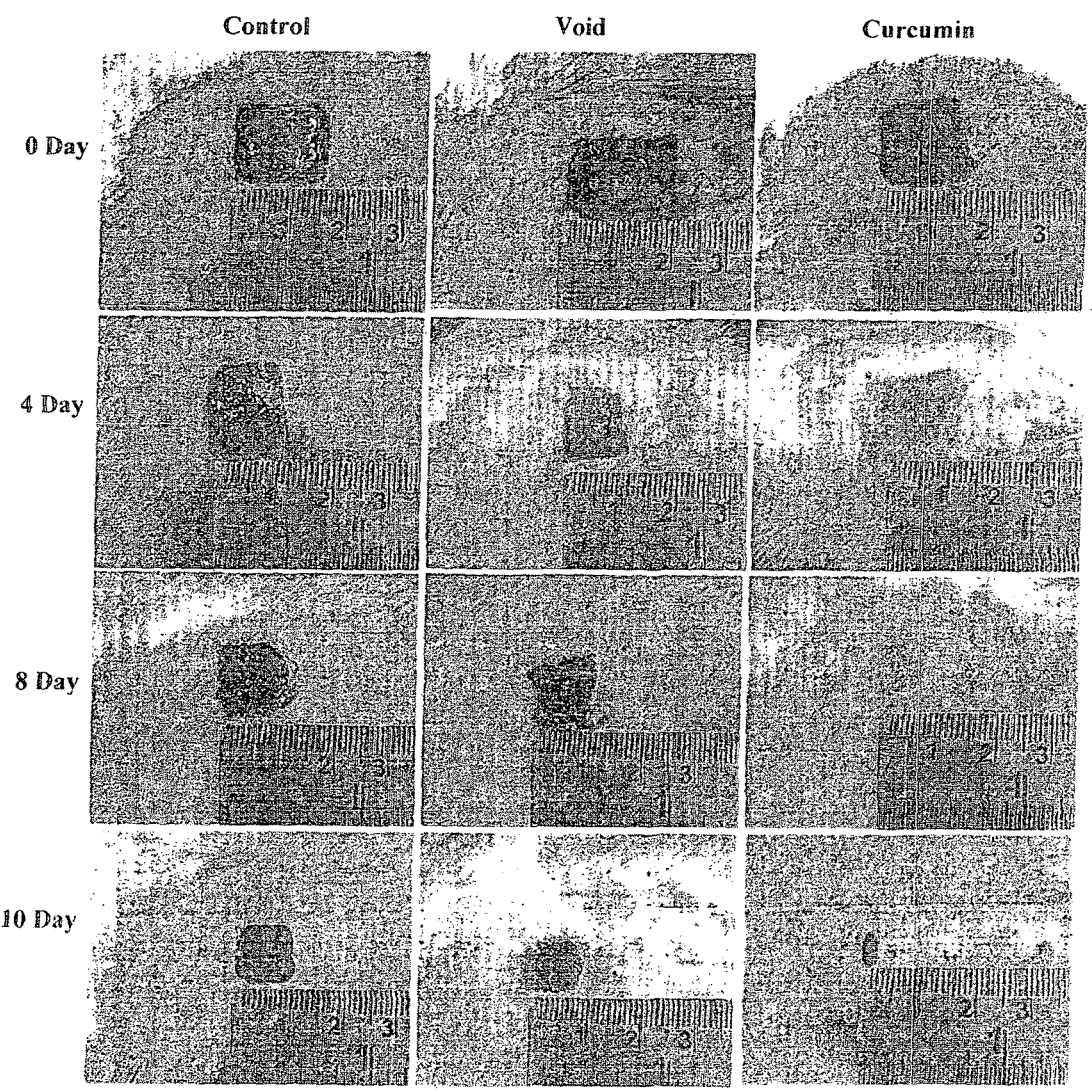

FIG. 4: shows photographical representation of contraction rate of wound covered with (a) cotton gauze as control, (b) void 1:2 alginate-chitosan sponge and (c) curcumin loaded 1:2 alginate-chitosan sponge at different post wounding day of our observation.

Figure 5:
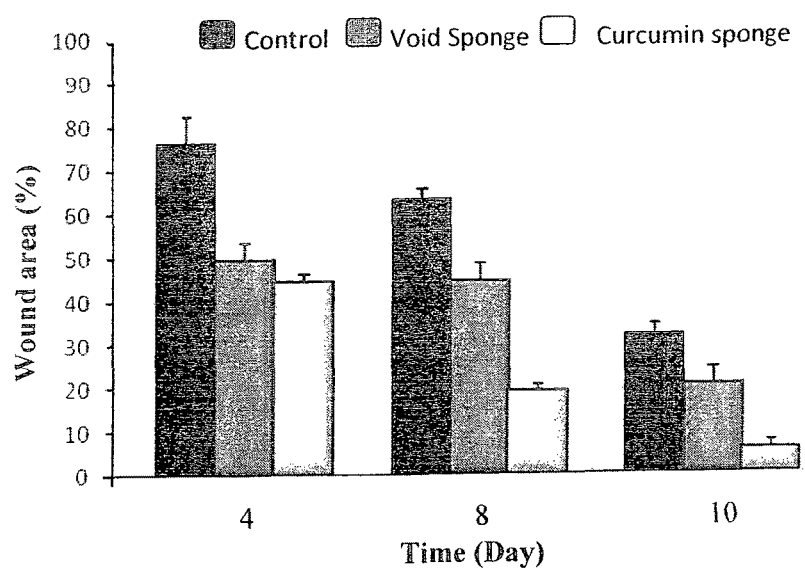

FIG. 5: shows total wound area of skin at different post wounding day as a percentage of original wound size.

DETAILED DESCRIPTION OF THE INVENTION

Preparation of Curcumin Encapsulated Chitosan-Alginate Sponge:

Briefly, Alginate solution (0.5% w/v) was prepared by dissolving sodium alginate powder (0.1 g) in 20 ml of deionised water at room temperature. Chitosan solution (0.5% w/v) was prepared by dissolving chitosan powder (0.1 g) in 20 ml of deionized water containing acetic acid (1.0% by weight) at room temperature. To form curcumin encapsulated AC Sponge, 50 mg of curcumin was incorporated in to fluid phase of 1.75 ml oleic acid. The oleic acid mixture was then emulsified with chitosan solution for 2 minute. The resultant solution was further homogenized (Biospacte Product Inc, Bartlesville, Okla.) for 3 minute with alginate solution. In this way, curcumin loaded AC sponge solution with different alginate: chitosan blend ratio (1:1, 1:2 and 1:3) were prepared (keeping curcumin and OA content constant) and pour out in a 6-well plate (well area: 9.6 cm$^2$). The suspension decant in 6 well plate was lyophilized for three days (−80° C. and <10 µm mercury pressure, LYPHLOCK, Labconco, Kansas City, Mo.) to get lyophilized sponge for further use.

Physicochemical Characterization of Chitosan-Alginate Sponges

Scanning Electron Microscope (SEM) Studies

The surface morphology of different formulation of curcumin encapsulated AC Sponge were characterized by SEM (JEOL JSMT220A scanning electron microscopy, MA) operating at an accelerating voltage of 10-30 Kv. The sponges were sputtered with gold to make them conductive and placed on a copper stub prior to the acquisition of SEM images.

Fourier Transform Infrared (FTIR) Spectral Study

FTIR spectra were taken in to observation (Perkin Elmer, Model Spectrum RX 1, USA) to investigate the possible chemical interactions between the curcumin and the AC sponge matrix. Native curcumin, alginate, chitosan, void sponge, different formulation of curcumin loaded sponge were crushed with KBr to get the pellets by applying a pressure of 300 kg/cm$^2$. FTIR spectra of the above sample were obtained by averaging thirty two interferograms with resolution of 2 cm$^{-1}$ in the range of 1000 to 4000 cm$^{-1}$.

Swelling Ability Study of Sponges

The swelling ability of different formulations of AC sponge was determined by equilibrium swelling study. The different formulation of sponges 1 cm×1 cm size were immersed in to PBS (0.01 M, PH 7.4). The weight of sponges was recorded every minute until equilibrium was reached. At each emersion interval, the samples were removed and the absorbed water gently removed with filter paper. The samples were then weighed immediately on a micro balance. Each experiment was repeated three times, and the average value was taken as the percentage water adsorption. The initial sample weight before immersion was recorded as $W_0$ and the sample weight after each immersion interval was recorded as $W_e$. The percent swelling at equilibrium $E_{SW}$ was calculated from the Flory-Huggins swelling formula:

$$E_{SW}(\%) = W_e - W_0/W_0 \times 100$$

In Vitro Degradation Study

The different formulation of AC sponges were incubated at phosphate-buffered saline (0.01 M, pH 7.4) with 500-1000 U/C.C. of lysozyme concentration in 6-well plate and kept at 37° C. [16]. At required period of time, the sponges were taken out, washed with deionized water, frozen, and lyophilized. The weights of the sponges were weighed in a microbalance and percentage of weight loss was calculated using the following equation:

$$\text{Weight loss (\%)} = (W_0 - W_t)/W_0 \times 100.$$

In Vitro Release Kinetics of Curcumin from Different Formulation of AC Sponge by (HPLC) Method In vitro release kinetics of curcumin from different formulations of curcumin loaded sponges were determined in PBS (0.01M, pH 7.4) with little modification. A total of 10 mg of curcumin-loaded chitosan-alginate sponge was suspended in 3 ml of PBS (0.01M, pH 7.4). It was mixed properly by vortexing and kept in a shaker at 37° C., rotating at 150 rpm in an orbit shaking incubator (Wadegati Lab equip, India). At predetermined time intervals, the samples were collected and replaced with same volume of fresh PBS (0.01 M, Ph 7.4). The collected samples were then subjected to centrifugation at 13, 800 rpm, 4° C. for 10 min (SIGMA 3K30, Germany) to obtain the supernatant containing released curcumin. The released curcumins profile was analysed using reverse phase isocratic mode (RP-HPLC) system of Waters™ 600, Waters Co. (Milford, Mass., USA) as described earlier [12]. For this, 20 µl of the sample was injected manually in the injection port and analyzed in the mobile phase consisting of a mixture of 60% acetonitrile and 40% citric buffer [1% (w/v) citric acid solution adjusted to pH 3.0 using 50% (w/v) sodium hydroxide solution] which was delivered at flow rate of 1 ml/min with a quaternary pump (M600E WATERS™) at 25° C. with a C 18 column (Nova-Pak, 150×4.6 mm, internal diameter). The curcumin levels were quantified by visible detector at 420 nm with dual wave length absorbance detector (M 2489). All measurements were performed in triplicates and the cumulative percentage of curcumin release was calculated and plotted versus time.

In Vivo Wound Healing Test

The Sprague-Dawley (SD) rats (160-180 g, 6 weeks) were used for wound healing test. The animals were anaesthetized intramuscularly by ketamine (100 mg/kg) and xylazine (10 mg/kg). The dorsal hair of the rats was removed. Full-thickness wound of 1.5×1.5 cm$^2$ was excised from the back of the rats. Each wound was covered with an equal size of curcumin loaded sponge, or void sponge, or cotton gauze for comparison. All wounds are covered with a piece of non adherent occlusive bandage. Treated rats were placed in individual cages, and the healing wounds were observed on the $0^{th}$, $4^{th}$, $8^{th}$ and $10^{th}$ days using a digital camera (Sony, cyber-shot, DSC-H9). The area of wound was calculated by measuring the length and breadth of the wound with digital slide calipers.

Results

Physicochemical characterization of chitosan-alginate sponges AC sponges were successfully prepared as a result of interaction in between positively charged chitosan and negatively charged sodium alginate. We have prepared three different formulations of sponge by varying alginate to chitosan in different ratio (1:1, 1:2 and 1:3) as shown in FIG. 1a. The resultant sponges were soft, light and fibrous in textures with adequate flexibility which will inevitably be required for in vivo applications.

Morphology Study

Scanning electron microscopy was employed to evaluate the morphological characteristics of the sponges. The cross section morphology of sponges appears porous and fibrillar structure in all the three formulations. However, it was observed that its morphology mainly depends on its alginate and chitosan content. To this end, we observed the sponge containing 1:1 ratio of alginate-chitosan was more irregular with highly interconnected cavities (FIG. 1b) compared to other formulation. Further, with increase in ratio of chitosan to alginate we found a gradual enlargement of pore size as seen in sponge matrix (FIG. 1b). This difference could be due to profound interanionic interaction between alginate and chitosan in sponge formulation containing equal proportionate of chitosan and alginate compared to other two formulations.

Fourier Transform Infrared (FTIR) Spectral Study

FTIR analysis was taken in to consideration to confirm the presence of curcumin in our AC sponge formulation as well as to examine any chemical (formation of chemical bonds) changes that might occurred in the polymer due to the addition of drug during the synthesis reaction. FIG. 2 shows the FTIR spectra's of alginate, chitosan, native curcumin void AC sponge and three different formulations of AC sponges. The characteristic band at 3434 cm$^{-1}$ can be attributed to —NH2 and —OH groups stretching vibrations in the chitosan matrix and a band for amide I at 1651 cm$^{-1}$ can be seen in the infrared spectrum of chitosan [18]. The alginate spectrum shows characteristic band of carbonyl (C=O) band at 1640 and 1424 cm$^{-1}$ [16]. The FTIR spectrum of native curcumin exhibited an absorption band at 3510 cm$^{-1}$ attributed to the phenolic O—H stretching vibration. Additionally, sharp absorption bands at 1605 cm$^{-1}$ (stretching vibrations of benzene ring of curcumin), 1510 cm-1 (C=O and C=C vibrations of curcumin), 1627 cm$^{-1}$ (C=C double bonds) and 1602 cm$^{-1}$ due to aromatic C=C double bonds. These marker peaks were also found in different formulation of AC sponges and were not noticed in void sponge, suggesting curcumin exist inside the sponge matrix. Similar results were also observed by Yallapu et al. and Mohanty et al. [12, 19]. Further, no shifting of these signature peaks, attributing curcumin could be present in dispersed condition in different formulation of AC sponges.

Water Uptake Ability

The ability of the sponge to absorb water is one of the important factors in determining its biological activity. Here we used PBS to evaluate the uptake ability (at 37° C.) as it mimics the body fluid and conditions. The percent swelling in three formulation of sponge are given in FIG. 3a. It was observed that all sample achieved equilibrium after immersion for 1 minute in to PBS solution. Similarly, all sponges exhibited good swelling as they had the ability to retain more water due to its high porous infrastructure. The result further demonstrated the sponge developed from alginate to chitosan ratio 1:1 (w/w proportion) showed minimum percent of swelling compared to other formulation. The 1:3 AC sponges showed a highest of about 35% and 1:2 sponges showed a medium of 31% water uptake ability. In contrast, the 1:1 AC sponge gave a minimum value of about 17% water uptake due to its micro porous configuration compared to other formulation.

In Vitro Degradation

Sponges used for wound healing should be biocompatible and biodegradable. Its degradation behavior is a crucial parameter needs to explain before imposing for long term dressing. So the percentage of weight loss of different formulation of sponges as a function of degradation time was taken in to observation and the results are presented in FIG. 3b. The in vitro degradation result degradation result demonstrated the weight loss for different formulation of AC sponges ranges from 22% to 65%. Further, it was observed that 1:1 AC sponge showed 1.3 and 2.8 times higher weight loss compared to 1:2 and 1:1 AC sponges respectively. This result indicated that 1:1 AC sponge was more stable compared to 1:2 and 1:3 sponges, probably because cross linking degree of 1:1 sponge was stronger than the others.

In Vitro Release Kinetics

Therapeutic efficiency of drug loaded sponges solely depends on the dose and released of the entrapped drug from its matrix at wound site. In this view, while observing the in vitro release profile, we observed a biphasic release pattern of entrapped curcumin from all sponge formulations used in our study (FIG. 3c). In 1:3 AC sponge, the burst release of curcumin (37.88±1.8%) was observed in first day which was followed by a slow and continuous release. Similarly, in 1:2 and 1:1 AC formulation, the release profile of curcumin was observed as 27.99±2.9 and 29.7±1.9% respectively in the first day followed by a slow and sustained release for a prolong time period of 10 days of our observation. The observed initial burst release might be due to the dissociation of surface absorbed drugs present in the polymeric matrix. Subsequently, sustained release activity of the drugs was due to the slow release of drugs entrapped inside the polymer matrix.

Wound Healing Test

After observing the in vitro release profile of curcumin from different formulation of AC sponges, we found 1:2 and 1:1 AC sponge formulation showed almost similar sustained release profile. However, 1:2 AC sponge formulations was chosen as suitable formulation for our wound healing experiment, because of its larger pore size and more water uptake ability compared to 1:1 formulation. This loose fabric structure or porosity could give proper ventilation to ensure no oxygen deficiency over the wound [20]. An ideal dressing sponge must achieve certain characteristics like good biodegradability, biocompatibility, slow sustained release of entrapped drug for longer time and moreover not to be associated with incidental adverse effects during healing process. In order to justify our formulated sponge's persuasive healing efficacy, in vivo healing studies were conducted with 1:2 AC sponge with or without curcumin. For control, the wound was covered with cotton gauze. The wound healing observation showed that on the $4^{th}$ postoperative day the cotton gauze adhered to wound surface and removal of it resulted in the loss of tissue and oozing of blood at the wound surface indicating tissues are under inflammation phase. However, AC sponge found to adhere at the wound surface and absorbed the bleed and exudation at the wound site. It suggests that the sponge containing alginate fiber absorbs the wound exudates to form a hydrogel protection layer that holds the moisture around the wound, on other hand chitosan enhances the infiltration of inflammatory cell and consequently accelerating wound cleaning. In this view, our observation also showed more healing of wound dressed with AC sponge compared to control. During dressing while removing the sponge from wound area, we have observed little bleeding and inflammation in void treated wound. In contrast, no sign of inflammation and oozing of blood with thicken underlying granulation tissue was marked in case of curcumin sponge treated wound, suggesting wound tissues are quickly preceded from inflammatory stage to proliferating stage. So, another prospective characteristic of using the AC sponge was its hydrogel layer which can reduces the frequency of dressing change (as it is biodegradable, biocompatible and absorbable) by holding the moisture around the wound. Further, the reduction in wound defect area was calculated by observing the wound area at various time intervals of our wound healing study.

From FIG. 4, the significant difference of wound closure was clearly marked in between the control and AC sponge treated groups on $4^{th}$ postoperative day. Conversely, we have not marked any significant difference of wound closure in void and curcumin treated sponge on the same day of our observation, suggesting irrespective of curcumin content our formulated AC sponge is a good absorbent and suitable substrate for better wound healing. The photograph further demonstrated curcumin sponge treated wound showed no sign of inflammation compared to control and void sponge treated wound, suggesting its early recovery from inflammation phase. This observation could be due to constant and profound release of anti inflammatory and anti infective drug curcumin from curcumin loaded AC sponge at wounded site. Similarly, on $8^{th}$ day post wounding, it was observed that with time curcumin sponge-treated wounds showed more healing response compared to void sponge and cotton gauze-treated wounds. While measuring the wound size we found the wound area of curcumin loaded AC sponge is almost half and one third of the void and cotton gauze treated wound area respectively (FIG. 5). On the $10^{th}$ postoperative day we observed the control, void sponge and curcumin sponge treated wounds contracted 68%, 80% and 94% respectively. It suggests though AC sponge is a good substrate showing better healing but curcumins anti oxidant and anti inflammatory properties accelerate the healing ability more profoundly with time. Thus, the results demonstrated curcumin loaded AC sponge may be useful as a therapeutic approach for better wound healing in near future.

The present study reveals that the mechanical release, water uptake, degradation and morphological properties of AC sponge are highly dependent on composition. The successful encapsulation of curcumin within AC sponge brought about a new avenue to improve the bioavailability of curcumin and can make the drug amenable for topical application in wound healing. Most importantly, the observed comprehensible results justified the curcumin loaded AC sponge was comparatively more effective than void AC sponge for wound healing therapeutic approach with time due to sustained drug retention and enhanced anti inflammatory effect.

We claim:

1. A process for preparing a curcumin encapsulated chitosan alginate sponge comprising the steps of:
   a) incorporating curcumin in a fluid phase of oleic acid to form a curcumin-oleic acid mixture, wherein the curcumin is encapsulated in oleic acid;
   b) subjecting the curcumin-oleic acid mixture to a step of emulsification with a chitosan solution by homogenization;
   c) emulsifying the homogenized solution formed in step b) with an alginate solution by homogenization; and
   d) lyophilizing the emulsion of step c) to produce a chitosan alginate sponge comprising curcumin encapsulated in oleic acid.

2. The process as claimed in claim 1, wherein the alginate solution is prepared by dissolving sodium alginate powder in deionized water at room temperature.

3. The process as claimed in claim 1, wherein the chitosan solution is prepared by dissolving chitosan powder in 20 ml of deionized water containing acetic acid at room temperature.

4. The process as claimed in claim 1, wherein the curcumin-oleic acid mixture is emulsified with the chitosan solution for 2 minutes.

5. The process as claimed in claim 1, wherein the homogenized solution formed in step b) is homogenized with the alginate solution for 3 minutes.

6. The process as claimed in claim 1, wherein the step of lyophilization is performed for 3 days at −80° C. and less than 10 μm mercury pressure.

7. The process as claimed in claim 1, wherein an alginate to chitosan weight ratio is selected from the group consisting of 1:1, 1:2 and 1:3.

8. The process as claimed in claim 1, wherein a weight ratio of alginate to chitosan is 1:2.

9. A sponge obtained by the process as claimed in claim 1, wherein a hydrophobic agent curcumin binds to a hydrophobic core of oleic acid.

10. The process as claimed in claim 1, wherein the curcumin encapsulated chitosan alginate sponge is suitable for application to a wounded skin to reinforce the skin for open wound repair.

11. A method for augmenting open wound repair comprising applying a wound dressing sponge prepared by the process of claim 1 to an open wound, wherein the wound dressing sponge comprises alginate to chitosan in a weight ratio of 1:2 and curcumin encapsulated in oleic acid, and is suitable for topical application.

12. The method as claimed in claim 11, wherein the sponge releases at least 40% of the encapsulated curcumin within 10 days of application to the wound.

13. The method as claimed in claim 12, wherein the sponge maintains at least 50% of its weight after 10 days of application to the wound.

14. The process as claimed in claim 1, wherein the process consists of the steps of:
  preparing an alginate solution by dissolving alginate powder in deionized water;
  preparing a chitosan solution by dissolving chitosan powder in deionized water;
  encapsulating curcumin in oleic acid to form encapsulated curcumin;
  emulsifying the chitosan solution with the encapsulated curcumin to form an emulsification;
  homogenizing the emulsification with the alginate solution to form a homogenized solution; and
  lyophilizing the homogenized solution.

* * * * *